United States Patent
Nioutsikou et al.

(10) Patent No.: US 11,850,023 B2
(45) Date of Patent: Dec. 26, 2023

(54) DETERMINING AN OUTER CONTOUR DURING MR IMAGING

(71) Applicant: Siemens Healthcare GmbH, Erlangen (DE)

(72) Inventors: Elena Nioutsikou, Erlangen (DE); Manuel Schneider, Erlangen (DE); Martin Requardt, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/950,295

(22) Filed: Sep. 22, 2022

(65) Prior Publication Data

US 2023/0093593 A1  Mar. 23, 2023

(30) Foreign Application Priority Data

Sep. 23, 2021 (DE) .......................... 102021210601.3

(51) Int. Cl.
*A61B 5/05* (2021.01)
*A61B 5/00* (2006.01)
*G06T 7/13* (2017.01)
*A61B 5/055* (2006.01)
*G01R 33/567* (2006.01)

(52) U.S. Cl.
CPC ............ *A61B 5/0037* (2013.01); *A61B 5/055* (2013.01); *A61B 5/704* (2013.01); *A61B 5/7292* (2013.01); *G01R 33/5673* (2013.01); *G06T 7/13* (2017.01); *G06T 2207/10088* (2013.01); *G06T 2207/30004* (2013.01)

(58) Field of Classification Search
CPC ..... A61B 5/0037; A61B 5/055; A61B 5/7292; G01R 33/5673
See application file for complete search history.

(56) References Cited

U.S. PATENT DOCUMENTS

| | | | |
|---|---|---|---|
| 2003/0081837 A1 | 5/2003 | Williame et al. | |
| 2005/0154291 A1 | 7/2005 | Zhao et al. | |
| 2006/0274885 A1* | 12/2006 | Wang | A61N 5/103 378/65 |
| 2012/0056621 A1 | 3/2012 | Blumhagen et al. | |
| 2015/0115963 A1* | 4/2015 | Huang | G01R 33/5611 324/322 |
| 2015/0355300 A1* | 12/2015 | Ooshima | G01R 33/5608 324/309 |
| 2016/0274202 A1* | 9/2016 | Stemmer | G01R 33/56563 |
| 2020/0258243 A1 | 8/2020 | Chang et al. | |

FOREIGN PATENT DOCUMENTS

CN  102419426 A  4/2012

* cited by examiner

*Primary Examiner* — Joel F Brutus
(74) *Attorney, Agent, or Firm* — Lempia Summerfield Katz LLC

(57) ABSTRACT

A magnetic resonance tomography unit and a method is provided in which a patient couch may be moved in relation to the longitudinal direction into the patient tunnel in the transversal direction into a left-hand side extreme position and an opposite-lying right-hand side extreme position. Using an image acquisition facility in the left-hand side extreme position a right-hand side part is acquired and in the right-hand side extreme position a left-hand side part of the outer contour of the predetermined object is acquired. Using the image acquisition facility, the outer contour of the object is subsequently created from the left-hand side part of the outer contour and also from the right-hand side part of the outer contour.

20 Claims, 4 Drawing Sheets

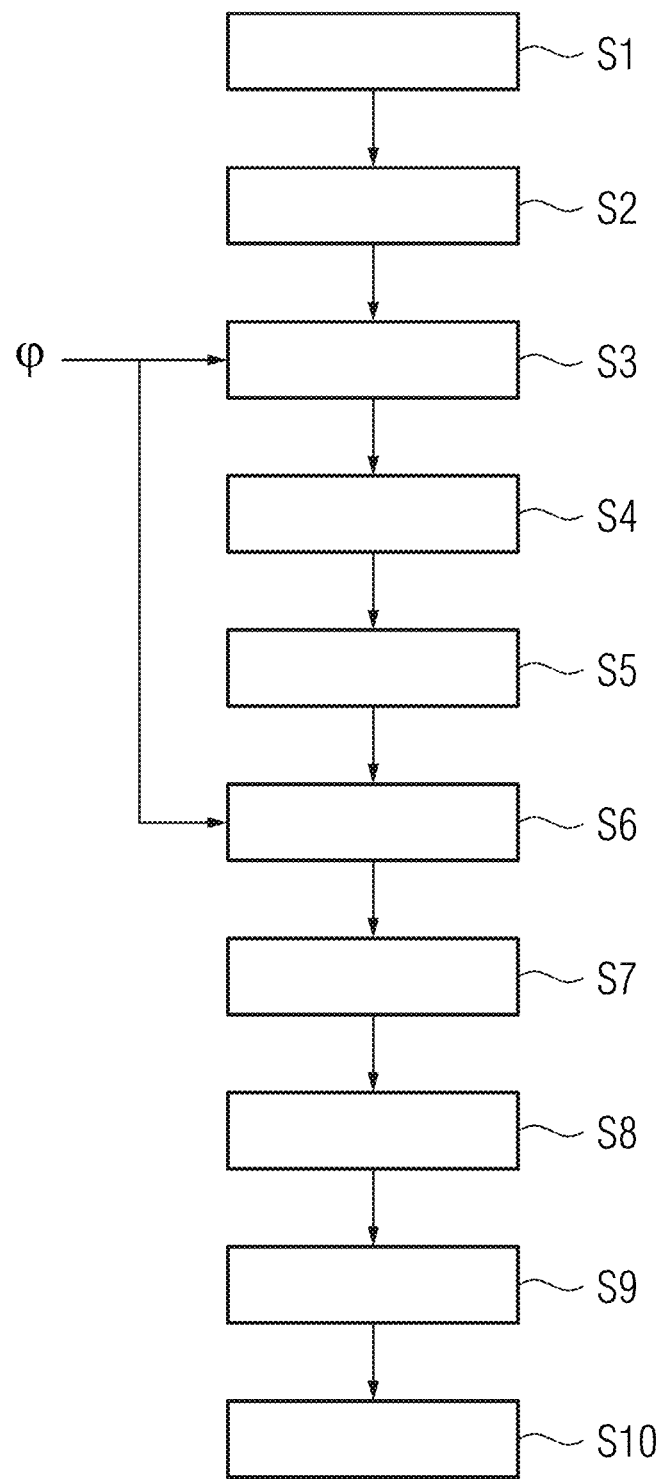

DETERMINING AN OUTER CONTOUR DURING MR IMAGING

CROSS REFERENCE TO RELATED APPLICATIONS

This application claims the benefit of DE 102021210601.3 filed on Sep. 23, 2021, which is hereby incorporated by reference in its entirety.

FIELD

Embodiments relate to a magnetic resonance tomography unit including a patient tunnel, which has a longitudinal direction and into which a predetermined object may be inserted, having a patient couch with which the predetermined object may be moved into the patient tunnel in the longitudinal direction, and having an image acquisition facility.

BACKGROUND

Magnetic resonance tomography units are imaging apparatuses that, to map an object to be examined (also referred to below in short as object or patient), orient nuclear spins of the object to be examined using an intense external magnetic field and excite the nuclear spins by an alternating magnetic field so as to precess around the orientation. The precession or return of the spins from the excited state into a state having less energy in turn generates as a response an alternating magnetic field that is received via antennas.

With the aid of magnetic gradient fields, a location encoding is impressed onto the signals and the location encoding subsequently renders it possible to allocate the received signal to a volume element. The received signal is then evaluated and a three-dimensional imaging representation of the object that is to be examined is provided. Local receiving antennas, so-called local coils, are used so as to receive the signal and the local coils are arranged directly on the object that is to be examined so as to achieve an improved signal-to-noise ratio. The receiving antennas may also be installed in a patient couch.

In radiotherapy, for example in the radiological treatment of tumors, an image of a patient is used as a basis for the treatment plan. Traditionally, computed tomography (CT) imaging is used for this purpose. However, on account of operational and financial advantages, operating procedures that are exclusively based on magnetic resonance (MR) are increasingly becoming preferred.

In order to be able to plan a therapy beam including sufficient dosimetric accuracy, the geometric accuracy of the patient model must be acceptable and even down to the skin of the patient. However, the broader the patient within the patient tunnel, the less acceptable the geometric accuracy with which the MR image may map the outer contour of the patient. The accuracy of MR images decreases namely from the inside out. The causes of this are in particular gradient non-linearity effects and DC field inhomogeneities or BO inhomogeneities.

Also, in the case of MRT devices including a patient tunnel that has an inner diameter of 80 cm, it is not possible to ensure that the outer contour of a patient is detected sufficiently precisely. On the contrary, experiments demonstrate that also in the case of large devices of this type in general only a relatively small spatial region (so-called field of view) may be sufficiently accurately represented if the patient lies on a flat table surface.

MR images are therefore still matched with CT images for treatment planning. The CT is so to speak the gold standard for geometric accuracy, so corresponding geometric fidelity may be guaranteed As pure MR operating processes enter clinical practice, users are looking for new methods in order to ensure the precision of patient positioning within the patient tunnel. Most users fall back on measurements of anthropomorphic phantoms in order to estimate the confidence level of the precision of a measurement near to the tunnel edges and then assume that this also applies for patients.

Others perform protracted sequences that incorporate the outer contour, that however leads to discomfort for the patient and often also leads to patient movements. Finally, devices for the monitoring of surfaces are used in the space and the devices support thermal technologies or optical methods.

A method for training a neural network to estimate a three-dimensional surface of a patient by machine learning is known from the publication US 2020/0258243 A1. The estimated surface is used in order to determine an isocenter of the patient. The estimated body regions are used in order to mark visible and invisible boundaries between body regions. The estimated body surface, the isocenter and the boundaries between body regions may be used in order to support the planning of image capture including an automatic patient positioning.

The publication US 2003/0081837 A1 describes a method for a computer in order to monitor changes in the position of an object. The method has the steps of calculating consecutive outlines by a dynamic contour modelling algorithm, wherein the contour modelling algorithm develops consecutive outlines and determines a correlation between consecutive contours in order to stop a reiteration of the algorithm if a correlation smaller than a predetermined value is determined.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments obtain the outer contour of an object or patient in MR imaging in a more simple or more comfortable manner.

Embodiments provide a magnetic resonance tomography unit including a patient tunnel, that has a longitudinal direction and into which a predetermined object may be inserted. The patient tunnel is also referred to as a patient tube or examination tube. The patient tunnel includes an approximately hollow cylindrical shape including a central axis that extends in the longitudinal direction of the patient tunnel. A predetermined object may be inserted into the patient tunnel for the purpose of an MRT examination. The object is for example a patient or a phantom. The object may also fundamentally be an industrial product, an animal and the like.

Moreover, the magnetic resonance tomography unit includes a patient couch with which it is possible to move the predetermined object in the longitudinal direction in the patient tunnel. The patient couch is to be understood here to be representative of any type of transport carriage with which it is possible to move an object in the examination tube or the patient tunnel. Usually, a patient lies on such a patient couch and is pushed into the patient tunnel or is automatically moved in the longitudinal direction of the patient tunnel.

Furthermore, the magnetic resonance tomography unit includes an image acquisition facility with which it is possible to obtain MR images of the predetermined object. The image acquisition facility in general includes suitable sensor technology (for example antennas), with which it is possible to receive corresponding MR signals, and also a data processing unit with which it is possible to generate the desired images from the MR signals.

The patient couch is configured in such a manner that it may be moved in relation to the longitudinal direction in the patient tunnel in the transversal direction into a left-hand side extreme position and an opposite-lying right-hand side extreme position. The patient couch may consequently be displaced in a perpendicular manner to the left-hand side and right-hand side with respect to the longitudinal direction. The patient that is lying on the patient couch may consequently also be moved in relation to their body axes to the left-hand side and right-hand side in the patient tunnel.

It is possible using the image acquisition facility to acquire a right-hand side image including a right-hand side part of an outer contour of the predetermined object from the predetermined object on the patient couch in the left-hand side extreme position. This means that the object, for example the patient, is moved on the patient couch entirely to the left-hand side. In this position, the right-hand side outer contour of the patient is closer to the center of the patient tunnel. In other words, the right-hand side part of the patient is located preferably in the high-resolution spatial region (also called the sweet spot) of the MRT device. In this position, it is possible to exactly detect the right-hand side part of the outer contour of the object by the MR imaging.

In the same manner, it is possible using the image acquisition facility to acquire a left-hand side image including a left-hand side part of an outer contour of the predetermined object from the predetermined object on the patient couch in the right-hand side extreme position. In a similar manner to the above-described acquisition of the right-hand side part of the outer contour, the left-hand side part of the outer contour may now be obtained by virtue of the fact that the object or the patient is pushed entirely towards the right-hand side. As a consequence, the left-hand side part of the patient is in the sweet spot, with the result that the left-hand side part of the outer contour may be obtained with a high degree of accuracy in the MR imaging.

Finally, it is possible to create accordingly the (entire) outer contour of the predetermined object from the left-hand side part of the outer contour and also from the right-hand side part of the outer contour. The left-hand side part of the outer contour and the right-hand side part of the outer contour may in other words be combined in an automated manner or in a semi-automated manner using the image acquisition facility. The desired outer contour is provided by the two parts.

The automated combination may be performed for example with the aid of landmarks. In particular, bones or tissue substances that are fixedly connected thereto (for example cartilage) may be used as such landmarks. The outer contour may relate to a slice of the MR imaging, in other words a 2D image. In this case, the outer contour includes, for example, a circular or oval shape for each body region. The outer contour may however also be viewed in a three-dimensional manner so that the outer contour is combined from the individual two-dimensional outer contours of the respective slices. It is therefore also possible to obtain a three-dimensional outer contour of the object from the three-dimensional (part) outer contours. In practice, then in the left-hand side extreme position, the slices of the right-hand side body part of the patient are recorded and in the right-hand side extreme position the slices of the left-hand side part of the body are recorded. Finally, the left-hand side 2D outer contours of the respective slices and the right-hand side 2D outer contours of the respective slices that are obtained as a result are combined to form a three-dimensional outer contour. Alternatively, in the case of block excitation, two 3D part outer contours may be obtained that in turn are accordingly combined in order to obtain the 3D outer contour.

In one embodiment, the image acquisition facility is configured so as to record examination images with a higher resolution than the left-hand side image and the right-hand side image. In this case, the left-hand side image and the right-hand side image that have the respective outer contours may be obtained with a somewhat reduced resolution with respect to conventional examination images. Owing to the reduced resolution, the left-hand side image and the right-hand side image or the left-hand side images and the right-hand side images may be acquired accordingly more rapidly (so-called quick scan).

In an embodiment, an image quality that may be achieved by the image acquisition facility in a spatial high-quality region in the patient tunnel is not below a predetermined level of quality. This spatial high-quality region represents the above-mentioned "sweet spot". In this high-quality region, for example, a minimum spatial resolution is provided. For example, the high-quality region may be distinguished by virtue of the fact that additional corrections are not required there.

In the case of an alternative embodiment, the image acquisition facility is configured so as to record the left-hand side and right-hand side image with such a high bandwidth that distortions on account of inhomogeneities of a B0 field of the magnetic resonance tomography unit do not exceed a predetermined level (for example at least 100 Hz per pixel). In the case of high bandwidths, in other words in the case of steep gradient fields, inhomogeneities accordingly have less of an impact. Bandwidths between 130 and 200 Hz per pixel may be used so that the spatial resolution between fat signals and water signals amounts to less than a pixel. Where applicable, bandwidths of 650 Hz or even up to 1000 Hz are also used. In the case of such high bandwidths, however, the noise proportion also disproportionately increases.

In one embodiment, the image acquisition facility may be configured so as to obtain the left-hand side and right-hand side image by 3D sequence excitation. In the case of this 3D sequence excitation, an entire block of the body of the object is excited. In this case, a flatter gradient may be used than in the case of 2D slice excitation. Advantageously, in the case of the 3D sequence excitation, interferences as a consequence of B0 inhomogeneities only occur in the readout direction and not in the stack direction of the slices as is the case in 2D sequence excitations.

In an embodiment, the image acquisition facility is configured so as to perform a compensating procedure (shimming) in each case prior to the acquisition of the left-hand side and the right-hand side image in order to optimize a homogeneity of the magnetic DC field of the magnetic resonance tomography unit for each of the acquisitions. The homogeneity of the magnetic DC field B0 is impaired by the presence of the object. Accordingly, in the situation when the object is pushed into the left-hand side extreme position, there is a different inhomogeneity of the DC field than in the situation in which the object is pushed into the right-hand side extreme position. It is therefore advantageous if after the respective displacement and prior to obtaining the MR image a respective compensating procedure is performed. Only in this manner is it possible to achieve a homogenous B0 field and therefore a high image quality.

The image acquisition facility may be configured so as in the case of the image acquisition of the left-hand side image and the right-hand side image to use non-cartesian, in particular radial, trajectories. These radial trajectories occur if the recording angle is tilted in each case by a specific angle. For example, radial trajectories have advantages in the case of such movements of the patient that are triggered by breathing. The radial technology in such situations has in particular preferences with respect to technologies that are based on cartesian coordinates.

The image acquisition facility may be configured so as to perform the image acquisitions of the left-hand side and right-hand side image in a specific breathing phase. As a consequence, it is possible to ensure that with regard to the breathing the left-hand side image also matches the right-hand side image. For this purpose, it is necessary that the image acquisitions are triggered according to the breathing rhythm.

The image acquisition facility may also be configured so as to record left-hand side and right-hand side images of the mentioned type in three spatial dimensions and a time dimension. As a consequence, a so-called 4D acquisition may also be achieved. Specifically, it is possible owing to this acquisition to detect movement of the outer contour of the object in the three-dimensional space. Extraordinarily precise data regarding time dimension is also therefore provided specifically for a therapy plan.

In an embodiment, the image acquisition is configured so as to automatically delete image points of an acquired anatomical image, that lie outside the outer contour. For example, in order to create a template for a radiotherapy plan, it is necessary to compensate an acquired anatomical image (2D or 3D) with a detected outer contour (2D or 3D). This means that the acquired anatomical image must be fitted exactly into the outer contour or superimposed with the outer contour. In this case, it may however occur that image points or portions of the acquired anatomical image protrude beyond the outer contour. In this case, the protruding portions or image points are automatically deleted. These parts that protrude beyond the outer contour are in general artifacts.

In addition, or alternatively, the image acquisition facility may also be configured so as to insert an acquired anatomical image into the outer contour and in this case so as to simulate image regions that are missing as fat and/or water. In the event therefore that the acquired anatomical image (2D or 3D) is fitted into the outer contour, it is feasible that the outer contour is larger than the acquired anatomical image. Gaps therefore appear that would not be filled in the combined image. Under no circumstances may these unfilled gaps be filled with air for example for radiotherapy, since air does not absorb the radiation, but common tissue types that are water and/or fat-based do. It is therefore advantageous if the image acquisition facility is capable of automatically filling gaps, that occur between the acquired anatomical image and the detected outer contour, with image portions or pixels that represent water or fat. In this manner, it is possible in particular to simulate the surface of a patient in a manner that is particularly realistic.

In one embodiment of the magnetic resonance tomography unit, the patient couch may be moved in the patient tunnel in the longitudinal direction into a front extreme position and an opposite-lying rear extreme position, using the image acquisition facility it is possible to acquire a rear image including a rear part of an outer contour of the predetermined object from the predetermined object on the patient couch in the front extreme position, using the image acquisition facility it is possible to acquire a front image including a front part of the outer contour of the predetermined object from the predetermined object on the patient couch in the rear extreme position, and using the image acquisition facility it is possible to create the outer contour of the predetermined object from the front part of the outer contour and the rear part of the outer contour.

The terms "front extreme position" and "rear extreme position" for example relate to the direction of insertion of the patient couch. In the front extreme position, the patient couch is pushed for example further into the patient tunnel than in the rear extreme position. The allocation may however also be inverted. The corresponding images are provided in the respective extreme positions.

The variations that are proposed above in conjunction with the embodiments of the magnetic resonance tomography unit, the patient couch of which may be displaced in the transversal direction into the two opposite-lying extreme positions "left-hand side" and "right-hand side" apply accordingly also for the magnetic resonance tomography unit, the patient couch of which may be displaced in the longitudinal direction into the two opposite-lying extreme positions "front" and "rear". In particular, the two embodiments may also be combined.

The above-mentioned object is also achieved by a method for detecting an outer contour of an object by a magnetic resonance tomography unit that includes a patient tunnel that has a longitudinal direction and into which the object is inserted, and also a patient couch with which the object may be moved in the longitudinal direction in the patient tunnel by moving the patient couch in relation to the longitudinal direction in the patient tunnel in the transversal direction into a left-hand side extreme position and an opposite-lying right-hand side extreme position, acquiring a right-hand side image including a right-hand side part of the outer contour of the object on the patient couch in the left-hand side extreme position, acquiring a left-hand side image including a left-hand side part of the outer contour of the object on the patient couch in the right-hand side extreme position and where the (entire) outer contour of the object is created from the left-hand side part of the outer contour and also from the right-hand side part of the outer contour.

The variations and advantages that are described above in conjunction with the magnetic resonance tomography unit also apply accordingly for the method. In this case, the functional features that are described may represent corresponding method steps.

Furthermore, a method is provided for creating an irradiation template by detecting an outer contour of an object as is described above. The method includes creating at least one contour of an organ of the object, that may be exposed to at most a predetermined radiation dose, in the outer contour. For example, nerves are particularly sensitive to irradiation. Nerves must therefore be accordingly identified in the template for radiotherapy. For example, the contour of a nerve is therefore created and is inserted into the outer contour, for example for the therapy plan. Where applicable, other organs that only withstand a small dose are accordingly marked or are inserted with their contour into the outer contour or the template. In certain circumstances, the contour of the irradiated object (for example tumor) may also be inserted into the outer contour. As a consequence, the irradiated object where applicable is better identified and may be better utilized as a template for a therapy plan.

In one embodiment of the method, the method furthermore has the steps: moving the patient couch in relation to the longitudinal direction into a front extreme position and an opposite-lying rear extreme position, acquiring a front image including a front part of the outer contour of the object on the patient couch in the rear extreme position, acquiring a rear image including a rear part of the outer contour of the object on the patient couch in the front extreme position and where the outer contour of the object is created from the front part of the outer contour and also from the rear part of the outer contour.

The variations that are proposed above in conjunction with the embodiments of the method for detecting an outer contour of an object by a magnetic resonance tomography unit, the patient couch of which may be displaced in the transversal direction into the two opposite-lying extreme positions "left-hand side" and "right-hand side", also apply accordingly for the method for detecting an outer contour of an object by the magnetic resonance tomography unit, the patient couch of which may be displaced in the longitudinal direction into the two opposite-lying extreme positions "front" and "rear". In particular, the two embodiments of the method may also be combined.

Embodiments include a computer program product that may be loaded directly into a processor of a programmable controller, including program code in order to implement all the steps of a method for operating a magnetic resonance tomography unit if the program product is executed on the controller.

Embodiments include a computer readable storage medium including electronically readable control information that is stored thereon, that is configured in such a manner that during use of the storage medium in a controller of a magnetic resonance tomography unit the control information carries out the method for operating a magnetic resonance tomography unit.

BRIEF DESCRIPTION OF THE FIGURES

The above-described characteristics, features, and advantages of this invention and also the manner in which these are achieved become clearer and more explicitly comprehensible in conjunction with the following description of the embodiments that are further explained in conjunction with the drawings.

FIG. 7 depicts a schematic block diagram of an embodiment of a method.

DETAILED DESCRIPTION

Figure 1:
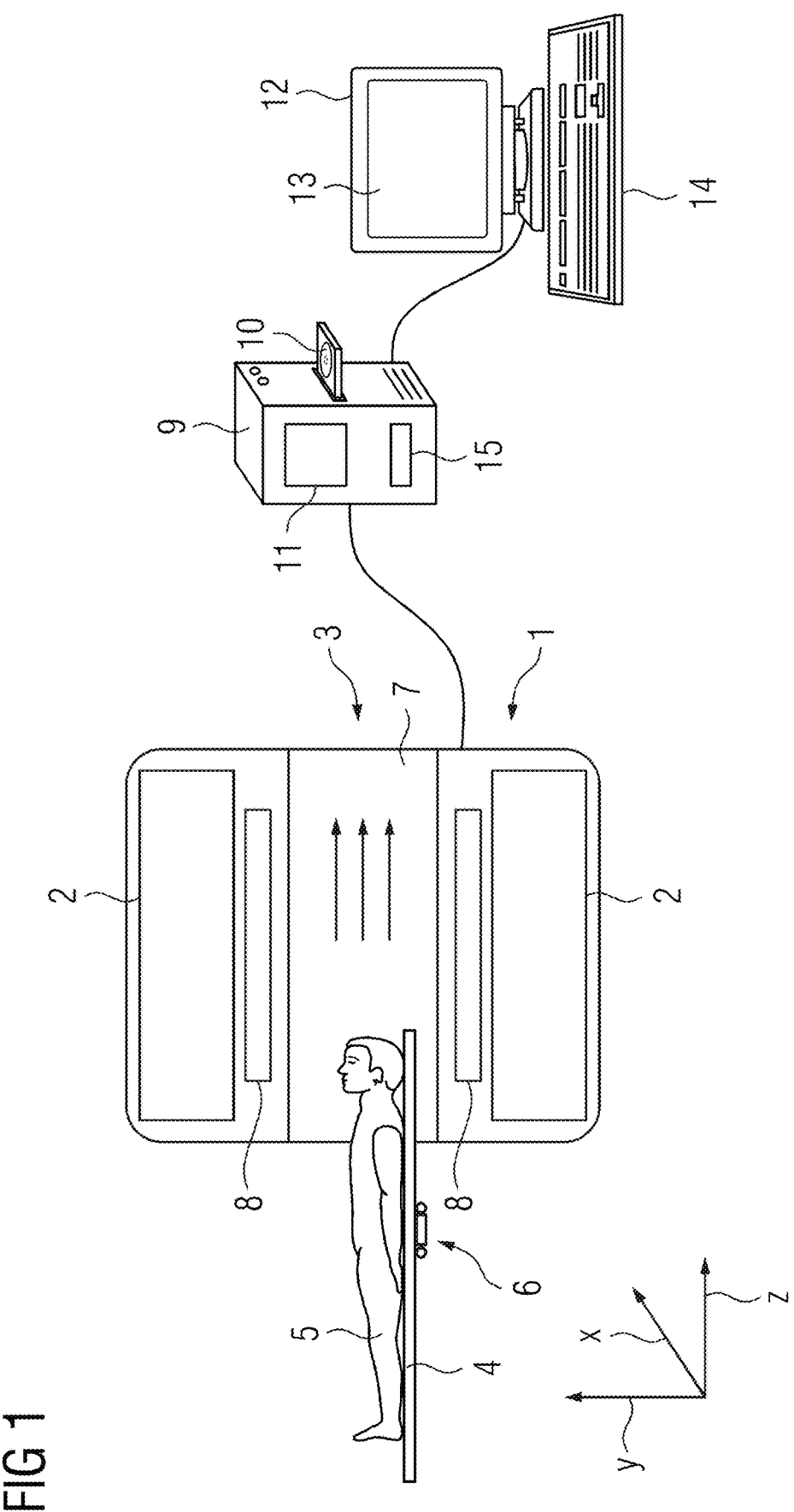
FIG. 1 depicts a schematic view of an MRT system according to an embodiment.

The embodiments that are further described below represent specific embodiments. In the figures, identical reference numerals refer to identical or similar elements. Furthermore, the figures are schematic illustrations of different embodiments. The elements that are illustrated in the figures are not necessarily illustrated to scale. On the contrary, these elements are reproduced in such a manner that their function and their purpose are comprehensible for the person skilled in the art. The connections that are illustrated in the figures between functional units or other elements may also be implemented as indirect connections, wherein a connection may be provided in a wireless or wire-connected manner. Functional units may be implemented as hardware, software or a combination of hardware and software.

FIG. 1 illustrates an embodiment of a magnetic resonance system (in the current document also referred to as a magnetic resonance tomography unit) for improved radiotherapy planning including a magnet apparatus 1, an image acquisition facility 9 (including an RF coil 9 for receiving an MR signal) and an input unit 14 and also an output unit 12 including a display element 13. A computer readable medium 10 (for example DVD, USB stick or the like) may be processed by the image acquisition facility 9. For example, a computer program is stored on the computer readable medium 10 and some of the steps of the method that is illustrated in FIG. 7 may be triggered or may be controlled using the computer program. The image acquisition facility 9 is accordingly configured in order to control or implement these method steps. For this purpose, the image acquisition facility 9 may have an evaluating facility 11 and also a control unit 15.

The MRT device and the magnet apparatus 1 in the following example includes a cryostat 2, in which a magnet made of superconducting material is located. Typically, such a cryostat 2 is filled with liquid helium in order to cool the magnet below the transition temperature and to transfer into the superconducting state. A superconducting magnet is a requirement in order to generate a high static magnetic field Bo 7 up to an intensity of multiple tesla in a large patient tunnel 3. The cryostat 2 and the magnet are typically essentially configured as a hollow cylinder in the hollow interior of which it is possible to generate the static magnetic field Bo 7. Furthermore, the magnet apparatus 1 includes RF coils 8 that surround the patient tunnel 3. The RF coils 8 are typically used both to send excitation signals as well as also to receive MR signals.

The patient 5 (in general: an object that is to be examined, where applicable a phantom) is moved by a patient couch 4 into the patient tunnel 3 for the examination using the MRT device. In order to record a tomographic image of the patient 5 using the MRT device 1 and to move the patient in a suitable manner, the patient couch includes a movement facility 6 with which the patient couch may be moved in the longitudinal direction z of the patient tunnel 3, however, also perpendicular thereto in the transversal direction x. Where applicable, a movement by the movement facility 6 in the y direction of a cartesian coordinate system (x-y-z) is also possible.

Figure 2:
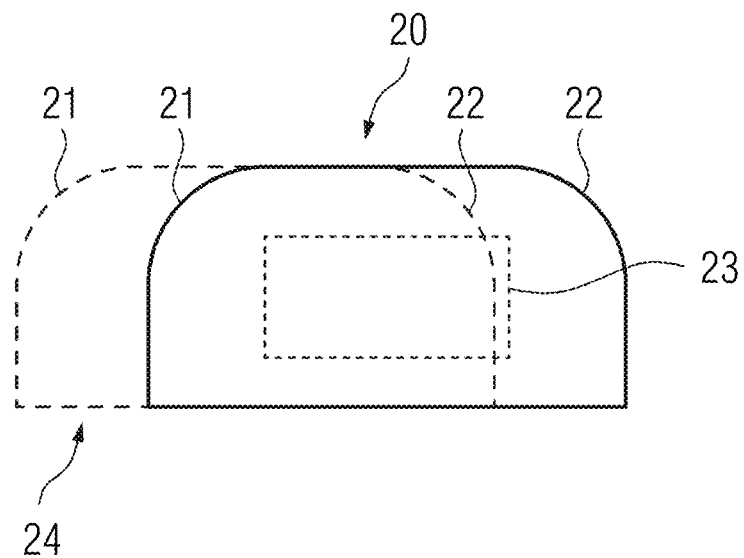
FIG. 2 depicts a schematic view of a transversal section of an outer contour of an object according to an embodiment.

FIG. 2 illustrates schematically a transversal section in the x-y plane through a patient 5. The patient 5 has at the section site, in other words in the corresponding slice, an outer contour 20. This outer contour includes a left-hand side part 21 of the outer contour and a right-hand side part 22 of the outer contour. A high-resolution region 23 (sweet spot) is illustrated within the outer contour 20 in FIG. 2. The high-resolution region 23 may be approximately spherical, cylindrical, cube-shaped or cuboid. For example, the high-resolution region has an edge length of 35 cm.

The problem is apparent in FIG. 2 that the outer contour 20 does not lie in the high-resolution region 23. As a consequence, the outer contour 20 during an MR recording is not illustrated sufficiently precisely in many cases.

At this point, embodiments record a (rapid) image capture in the sequence protocol of the image capturing facility in which the patient couch 4 moves for example from the left-hand side to the right-hand side and in this case assumes a left-hand side extreme position and a right-hand side extreme position. In FIG. 2, the left-hand side extreme position 24 is illustrated using dashed lines. As is apparent, a right-hand side part 22 of the outer contour (at least in part) now extends through the high-resolution region 23.

As a consequence, at least the right-hand side part 22 of the outer contour (insofar as in the sweet spot) may be represented particularly precisely with the aid of the MR imaging.

In a similar manner, the patient may be moved by the patient couch 4 into a right-hand side extreme position, that is not illustrated in FIG. 2 for the sake of clarity. In this right-hand side extreme position, the left-hand side part 21 of the outer contour (at least in part) extends through the high-resolution region 23. Consequently, at least the left-hand side part 21 of the outer contour (insofar as in the sweet spot) may be represented particularly precisely.

The images that are acquired in the two extreme positions may now be combined in an automated manner or in a part-automated manner with the aid of the image acquisition facility 9. The combination may be performed with reference to landmarks (for example bones), whereby a particularly precise outer contour 20 of the patient may be obtained.

In detail, the patient 5 is pushed from the center outwards or from one extreme position into the other extreme position with the result that the left-hand side or right-hand side outer surface of the patient (at least in part) is located in the high-resolution region 23 of the static main magnetic field 7 and the gradient system. This ensures a minimal distortion and an exact representation of the corresponding region of the body contour in the case of full resolution. Subsequently, a further image capture is performed at the opposite-lying end, in other words in the other extreme position, in order to map the two sides of the patient with a high degree of geometric accuracy. The two images are then combined. The overlaps of the images are taken into consideration.

In order to further reduce distortions on account of BO inhomogeneities (on account of inhomogeneities of the static main field 7 or on account of BO susceptibility artifacts), the (rapid) image acquisition is preferably performed with a particularly high readout bandwidth (>100 Hz per pixel). Furthermore, a 3D sequence may be used for the excitation of an entire block since, in this case, distortions on account of BO inhomogeneities only occur in the readout direction and not in the direction of the slice selection as in the case of 2D sequences.

Prior to each of the two scans in the extreme positions a separate shimming procedure may be performed so as to compensate BO inhomogeneities. For this reason, the adaptation volume, that corresponds to the regions that are used for the calculation of the shimming current, is positioned around the side of the patient that is currently being scanned so as to determine the body contour or outer contour.

From a technical point of view, the body contour scan may either be performed prior to or after the rest of the protocol of the MRT image acquisition. The body contour scan may be performed at the start in order to facilitate the allocation of the clinical scan (examination images).

The method described above may be implemented using a patient couch that is not only capable of moving the patient into and out of the patient tunnel 3 in a conventional manner in the z-direction but rather also allows transversal movements (x-direction) within the patient tunnel 3. Alternatively, the patient 5 may be positioned on a floating couch that generally renders possible displacements in the x-z plane. If the movements of the patient couch cannot be controlled precisely, the two images that are recorded may overlap and a local, rigid registration (landmark) may be performed in the region of the overlap.

Alternatively, or in addition thereto, in other words the patient may be displaced in the z-direction in order to record two images that are offset in the z-direction (where applicable in lieu of a left-hand side/right-hand side image that is offset in the x-direction). Consequently, FOV limitations could be compensated in the z-direction.

In particular in the case of applications in the abdomen, in the pelvis or in the thorax, it may be necessary to appropriately take breathing movements into consideration. In this case, a rapid contour scan may be performed with the aid of a movement-robust non-cartesian radial trajectory while the patient is breathing freely. In comparison to conventional cartesian sequences that suffer from movement artifacts, movement artifacts in images of radial sequences appear in the form of fewer noticeable blurs. An increased accuracy of the body contour may be achieved in that the radial sequence that is applied while breathing freely is combined with a respiratory "motion gating" (movement management). This renders it possible to calculate the outer body contour in a specific breathing phase or to estimate 4D body contour images (three spatial dimensions and a time dimension). Alternatively, the patients may be instructed during a conventional cartesian image recording to hold their breath (to breathe in or out).

Figure 3:
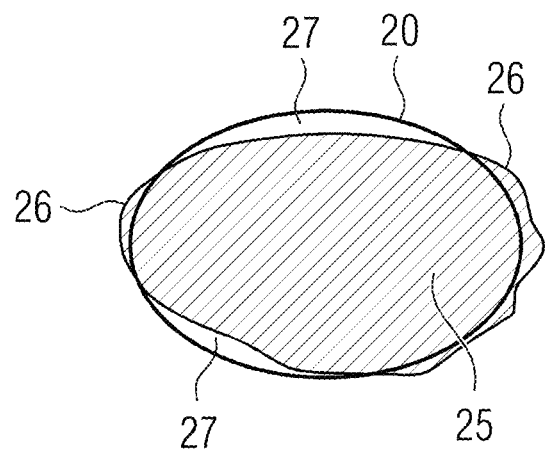
FIG. 3 depicts a superimposition of an outer contour and an MRT image according to an embodiment.
Figure 4:
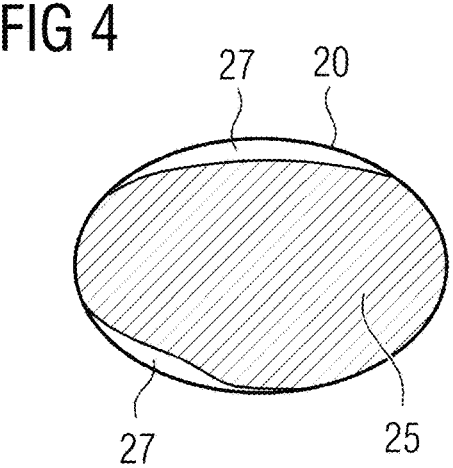
FIG. 4 depicts the superimposition of FIG. 3 with a section of an MR image according to an embodiment.
Figure 5:
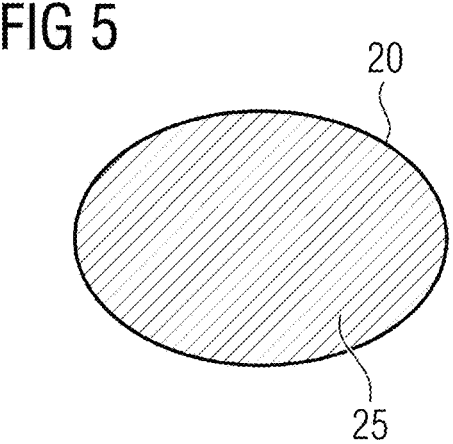
FIG. 5 depicts the section of the MR image of FIG. 4 with filled image portions according to an embodiment.

In order to obtain information that is required for the treatment plan for example for a radiation therapy with reference to anatomical MR simulation images, in general two operating steps are required that are now explained in conjunction with FIGS. 3 to 5. The starting point is an anatomical MR image 25 that has a low geometric accuracy and a loss of resolution in the edge regions. Its outer contour does not correspond to the actual outer contour 20 of the object or the patient 5. In the example of FIGS. 3 to 5, the outer contour 20 is selected as oval in contrast to the example from FIG. 2. The actual precise outer contour 20 is determined using the above-described method. The anatomical MR image 25 and the actual outer contour 20 are oriented with respect to one another for example by landmarks as is depicted in FIG. 3. In this case, protruding image regions 26 occur in which the anatomical MR image 25 protrudes beyond the outer contour 20. Moreover, gaps 27 occur in which the anatomical MR image 25 does not reach the outer contour 20.

The anatomical MR image therefore has boundary regions, in other words protruding image regions 26 that are incorrectly represented as tissue (fat or water) rather than as air. Therefore, initially the anatomical MR image 25 is cut as is illustrated in FIG. 4. The protruding image regions 26 are cut or deleted. Consequently, the image information is limited to the precise outer contour 20.

Since edge regions (gaps 27) may also occur in the anatomical MR images 25 and the edge regions are incorrectly represented as air rather than tissue (fat or water), a filling operation is performed in a second step. As a consequence, the remaining gaps 27 between the acquired anatomical MR image 25 and the determined outer contour 20 are filled in accordance with FIG. 5. It is preferred that these gaps are filled with fat-equivalent voxels since this is the most likely tissue type that is located under the skin. From a dosimetry point of view, the differences in the X-ray absorption between tissue types such as water and fat are small and may be ignored in the view of the advantages that the precise contours offer in the case of the treatment plan.

Figure 6:
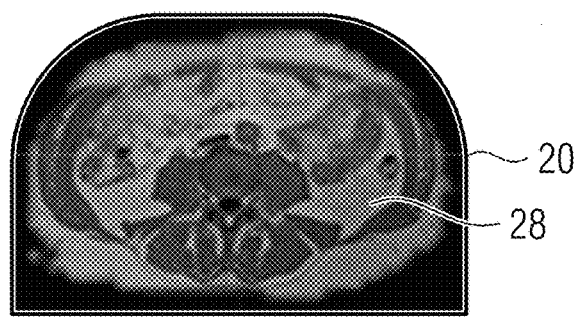
FIG. 6 depicts an outer contour including an MR image of a patient fitted inside it according to an embodiment.

For clarification, FIG. 6 illustrates an actual MR recording 28. The outer contour of this actual MR recording 28 is imprecise. Therefore, the outer contour 20 of the patient is determined separately, as this is described above. In the present example, the outer contour 20 is selected in the form of the outer contour of FIG. 2. The voxels that are located between the outer contour 20 and the actual MR recording 28 may be filled with fat-equivalent voxels.

FIG. 7 illustrates schematically a flow diagram of an embodiment of a method. The method is used so as to detect an outer contour of an object, for example of a patient, by a magnetic resonance tomography unit that includes a patient tunnel 3, that includes a longitudinal direction and into which the object is inserted, and also a patient couch 4 with which the object may be moved in the longitudinal direction in the patient tunnel 3. In a first step S1, the patient couch 4 is moved in relation to the longitudinal direction z in the patient tunnel 3 in the transversal direction x into a transversal extreme position. For example, the transversal movement in the x-direction is delimited in a manner relating to hardware or software technology in the two opposite directions owing to corresponding extreme positions, namely a left-hand side extreme position and a right-hand side extreme position. For example, in step S1, the patient couch is moved into the left-hand side transversal extreme position. In an optional step S2, a compensation (shimming) of the DC field is performed with the result that it is possible to achieve a homogenous BO field when the patient is in this extreme position.

In a subsequent step S3, a right-hand side image including a right-hand side part of an outer contour of the object on the patient couch is acquired in the left-hand side extreme position. In the event that the region of the object or patient that is to be recorded is moved on account of the patient breathing, it may be favorable to only perform the acquisition during a specific breathing phase φ. This breathing phase φ is provided for example by the control unit 15.

In a step S4, the patient couch is now moved towards the right-hand side in the transversal direction into its right-hand side transversal extreme position. Optionally, in step S5 a compensation of the DC field may also be performed so as to increase the homogeneity of the DC field.

In this right-hand side transversal extreme position, in accordance with step S6 a left-hand side image is now acquired including a left-hand side part of the outer contour of the object on the patient couch. A left-hand side part and a right-hand side part of the outer contour of the object is now provided. The two parts may be joined together in a step S7 to an entire outer contour of the object.

In a step S8 an anatomical MR image is superimposed with the entire outer contour. If a part of the anatomical MR image lies outside the entire outer contour during this superimposition, this image section that lies outside is cut or deleted.

Conversely, if gaps occur in the case of the superimposition of the anatomical MR image with the entire outer contour, it is possible to fill the gaps in step S9. It is preferred that the gaps are filled with water-equivalent or fat-equivalent voxels or pixels.

The three-dimensional MR image, that is obtained in this manner and which where applicable is cut and/or synthetically filled, may be used as a basis for the creation of a therapy plan in accordance with step S10 for radiation therapy.

In an advantageous manner, the above-described method for determining an outer contour of an object is robust and may be used rapidly. Moreover, it minimizes errors that occur on account of the discomfort of the patient. It provides security if clinical routines are to include only MR operating processes. Even in the case of large patients, additional expensive surface monitoring devices are not required. Since the CT detection is avoided, the known advantages of a simulation apply with only one imaging modality.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography unit comprising:
 a patient tunnel including a longitudinal direction and into which a predetermined object is inserted;
 a patient couch with which the predetermined object is moved in the longitudinal direction in the patient tunnel, wherein the patient couch is configured to be moved in relation to the longitudinal direction in the patient tunnel in a transversal direction into a left-hand side extreme position and an opposite-lying right-hand side extreme position; and
 an image acquisition facility configured to acquire a right-hand side image including a right-hand side part of an outer contour of the predetermined object from the predetermined object on the patient couch in the left-hand side extreme position, the image acquisition facility configured to acquire a left-hand side image including a left-hand side part of the outer contour of the predetermined object from the predetermined object on the patient couch in the right-hand side extreme position, the image acquisition facility configured to create the outer contour of the predetermined object from the left-hand side part of the outer contour and also from the right-hand side part of the outer contour.

2. The magnetic resonance tomography unit of claim 1, wherein the image acquisition facility is configured to record examination images with a higher resolution than the left-hand side image and the right-hand side image.

3. The magnetic resonance tomography unit of claim 1, wherein an image quality that is achieved by the image acquisition facility in a spatial high-quality region in the patient tunnel is not below a predetermined level of quality.

4. The magnetic resonance tomography unit of claim 1, wherein the image acquisition facility is configured to record the left-hand side image and right-hand side image with such a high bandwidth that distortions on account of inhomogeneities of a B0 field of the magnetic resonance tomography unit do not exceed a predetermined level.

5. The magnetic resonance tomography unit of claim 1, wherein the image acquisition facility is configured so as to obtain the left-hand side image and right-hand side image by 3D sequence excitation.

6. The magnetic resonance tomography unit of claim 1, wherein the image acquisition facility is configured so as to perform a compensating procedure in each case prior to the acquisition of the left-hand side image and the right-hand side image to optimize a homogeneity of a magnetic DC field of the magnetic resonance tomography unit for each of the acquisition of the left-hand side image and the right-hand side image.

7. The magnetic resonance tomography unit of claim 1, wherein the image acquisition facility is configured to acquire the left-hand side image and the right-hand side image using non-cartesian trajectories.

8. The magnetic resonance tomography unit of claim 7, wherein the non-cartesian trajectories are radial trajectories.

9. The magnetic resonance tomography unit of claim 1, wherein the image acquisition facility is configured to perform the image acquisitions of the left-hand side image and right-hand side image during a same specific breathing phase.

10. The magnetic resonance tomography unit of claim 1, wherein the image acquisition facility is configured to record left-hand side and right-hand side images in three spatial dimensions and a time dimension.

11. The magnetic resonance tomography unit of claim 1, wherein the image acquisition facility is configured to automatically delete image points of an acquired anatomical image that lie outside the outer contour.

12. The magnetic resonance tomography unit of claim 1, wherein the image acquisition facility is configured to insert an acquired anatomical image into the outer contour or to superimpose the acquired anatomical image and the outer contour to simulate image regions that are missing as fat, water, or fat and water.

13. The magnetic resonance tomography unit of claim 1, wherein the patient couch is moved in the patient tunnel in the longitudinal direction into a front extreme position and an opposite-lying rear extreme position;
  wherein the image acquisition facility is configured to acquire a rear image including a rear part of the outer contour of the predetermined object from the predetermined object on the patient couch in the front extreme position;
  wherein the image acquisition facility is configured to acquire a front image including a front part of the outer contour of the predetermined object from the predetermined object on the patient couch in the rear extreme position; and
  wherein the image acquisition facility is configured to create the outer contour of the predetermined object from the front part of the outer contour and the rear part of the outer contour.

14. A method for detecting an outer contour of an object by a magnetic resonance tomography unit that includes a patient tunnel that has a longitudinal direction and into which the object is inserted and a patient couch with which the object is moved in the longitudinal direction in the patient tunnel, the method comprising:
  moving the patient couch in relation to the longitudinal direction in the patient tunnel in a transversal direction into a left-hand side extreme position and an opposite-lying right-hand side extreme position;
  acquiring a right-hand side image including a right-hand side part of the outer contour of the object on the patient couch in the left-hand side extreme position;
  acquiring a left-hand side image including a left-hand side part of the outer contour of the object on the patient couch in the right-hand side extreme position; and
  creating the outer contour of the object from the left-hand side part of the outer contour and from the right-hand side part of the outer contour.

15. The method of claim 14, further comprising:
  creating at least one contour of an organ of the object that is exposed to at most a predetermined radiation dose, in the outer contour.

16. The method of claim 14, further comprising:
  moving the patient couch in relation to the longitudinal direction into a front extreme position and an opposite-lying rear extreme position;
  acquiring a front image including a front part of the outer contour of the object on the patient couch in the rear extreme position;
  acquiring a rear image including a rear part of the outer contour of the object on the patient couch in the front extreme position; and
  creating the outer contour of the object from the front part of the outer contour and also from the rear part of the outer contour.

17. A non-transitory computer implemented storage medium, including machine-readable instructions stored therein, that when executed by at least one processor, cause the processor to:
  moving a patient couch in a patient tunnel of a magnetic resonance tomography unit, that has a longitudinal direction and into which an object is inserted, in relation to the longitudinal direction in the patient tunnel in a transversal direction into a left-hand side extreme position and an opposite-lying right-hand side extreme position;
  acquiring a right-hand side image including a right-hand side part of an outer contour of the object on the patient couch in the left-hand side extreme position;
  acquiring a left-hand side image including a left-hand side part of the outer contour of the object on the patient couch in the right-hand side extreme position; and
  creating the outer contour of the object from the left-hand side part of the outer contour and from the right-hand side part of the outer contour.

18. The non-transitory computer implemented storage medium of claim 17, further comprising:
  acquiring examination images with a higher resolution than the left-hand side image and the right-hand side image.

19. The non-transitory computer implemented storage medium of claim 17, wherein an image quality in a spatial high-quality region in the patient tunnel is not below a predetermined level of quality.

20. The non-transitory computer implemented storage medium of claim 17, wherein the left-hand side image and right-hand side image are acquired with such a high bandwidth that distortions on account of inhomogeneities of a B0 field of the magnetic resonance tomography unit do not exceed a predetermined level.

* * * * *